(12) United States Patent
Schwarz et al.

(10) Patent No.: US 6,673,960 B1
(45) Date of Patent: Jan. 6, 2004

(54) WORK-UP OF DISTILLATION RESIDUES FROM THE SYNTHESIS OF TOLUENE DIISOCYANATE

(75) Inventors: Hans Volkmar Schwarz, Waterloo (BE); Markus Maurer, Ludwigshafen (DE); Michael Sander, Ruhland (DE); Eckhard Ströfer, Mannheim (DE); Rene Leuthold, Hohenbocka (DE); Burghard Hantel, Cosel (DE); Siegfried Richter, Schraden (DE); Jörg Therre, Worms (DE)

(73) Assignee: BASF Aktiengesellschaft, Ludwigshaften (DE)

( * ) Notice: Subject to any disclaimer, the term of this patent is extended or adjusted under 35 U.S.C. 154(b) by 0 days.

(21) Appl. No.: 09/719,616

(22) PCT Filed: Jun. 2, 1999

(86) PCT No.: PCT/EP99/03812

§ 371 (c)(1),
(2), (4) Date: Dec. 14, 2000

(87) PCT Pub. No.: WO99/65868

PCT Pub. Date: Dec. 23, 1999

(30) Foreign Application Priority Data

Jun. 18, 1998 (DE) .......................... 198 27 086

(51) Int. Cl.[7] ................... C07C 265/00; C07C 263/00; C07C 209/00
(52) U.S. Cl. ................... 560/330; 560/348; 560/347; 560/351; 560/352; 564/414; 564/422
(58) Field of Search ................... 560/347, 352, 560/351, 348, 330; 564/422, 414

(56) References Cited

U.S. PATENT DOCUMENTS

| | | | | |
|---|---|---|---|---|
| 3,128,310 A | * | 4/1964 | Koch | 564/414 |
| 3,210,395 A | * | 10/1965 | McDougall | 564/414 |
| 3,331,876 A | * | 7/1967 | Horn et al. | 560/347 |
| 3,499,021 A | | 3/1970 | Kober et al. | |
| 3,499,035 A | | 3/1970 | Kober et al. | |
| 3,694,323 A | | 9/1972 | Cooper et al. | |
| 4,000,099 A | | 12/1976 | Nemoto et al. | |
| 4,032,574 A | * | 6/1977 | Keshi et al. | 564/326 |
| 4,091,009 A | | 5/1978 | Cassata | |
| 4,137,266 A | * | 1/1979 | Cassata | 564/414 |
| 4,143,008 A | | 3/1979 | Zwolinski et al. | |
| 4,289,589 A | | 9/1981 | Koehler | |
| 4,311,800 A | * | 1/1982 | Reishl | 521/109.1 |
| 4,422,976 A | * | 12/1983 | Yamamoto et al. | 560/347 |
| 4,654,443 A | * | 3/1987 | Marks et al. | 564/305 |

FOREIGN PATENT DOCUMENTS

| | | |
|---|---|---|
| DE | A-27 03 313 | 1/1977 |
| DE | 29 42 678 A1 | 10/1979 |
| DE | A-296 088 | 7/1986 |
| DE | A-257 827 A1 | 2/1987 |
| DE | A-42 11 774 A1 | 4/1992 |
| EP | A-0 017 972 | 10/1980 |
| JP | 58-201 751 | 11/1983 |
| JP | 09151270 A | 6/1997 |

\* cited by examiner

*Primary Examiner*—Alan L. Rotman
*Assistant Examiner*—Taylor V Oh
(74) *Attorney, Agent, or Firm*—Fernando A. Borrego

(57) ABSTRACT

A process for working up distillation residues from the synthesis of tolylene diisocyanate by reaction of the distillation residues with water comprises reacting the TDI distillation residues with water in a continuous or semicontinuous process in a backmixed reactor in the presence of hydrolysate.

16 Claims, 1 Drawing Sheet

WORK-UP OF DISTILLATION RESIDUES FROM THE SYNTHESIS OF TOLUENE DIISOCYANATE

Figure 1:
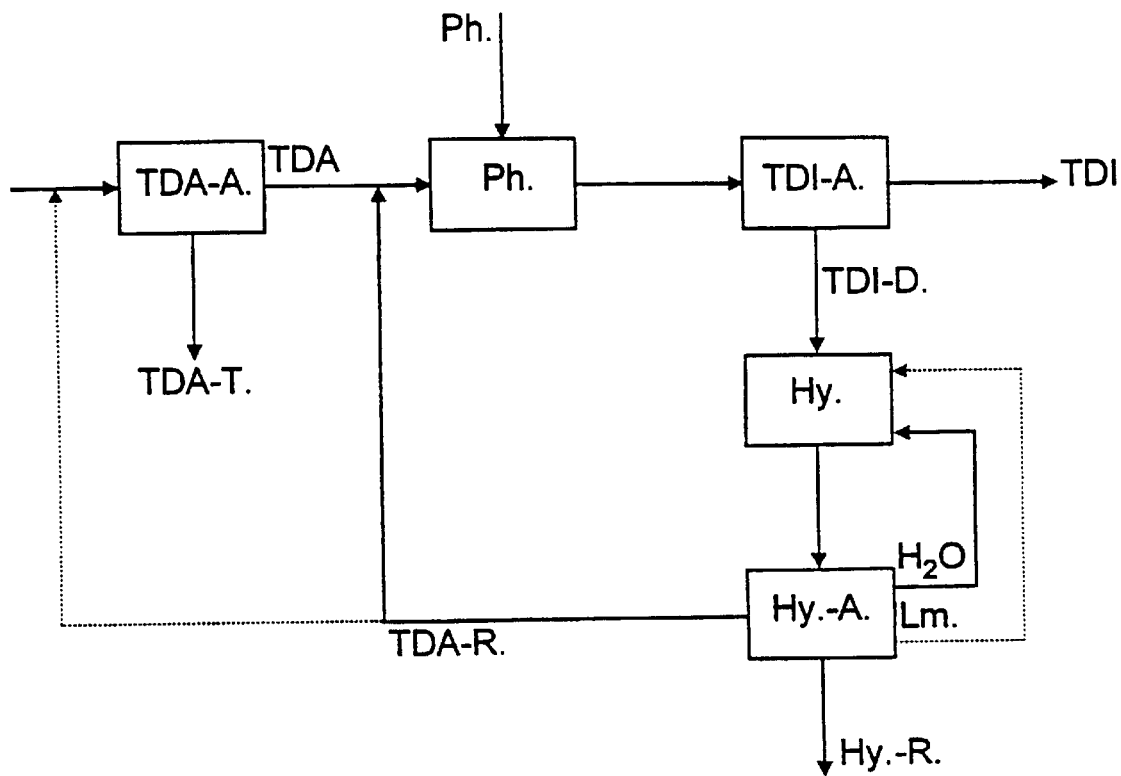

Work-up of distillation residues from the synthesis of tolylene diisocyanate

The present invention relates to a process for working up distillation residues from the synthesis of tolylene diisocyanate.

Tolylene diisocyanate (TDI) is used in large quantities for producing polyurethanes. TDI is usually prepared by reacting toluenediamine (TDA) with phosgene. This process has been known for a long time and has been extensively described in the literature.

In this process, the TDA is customarily reacted with phosgene in a conventional two-stage phosgenation.

However, there are other syntheses in which TDI is prepared by dissociation of a urethane synthesized from TDA, urea and alcohol or by some other route.

In all these cases, the synthesis ends with a distillation step in which the TDI is separated from by-products. The ratio of TDI to residue from this distillation step can be from 1 to 20%. There is therefore a considerable economic incentive to make use of the materials in this residue.

The prior art describes various processes for the direct utilization of materials in residues from the preparation of TDI.

In U.S. Pat. No. 3,499,021, the residue is phosgenated and returned to the process. In DE-A-42 11 774, DD-A-257 827 and U.S. Pat. No. 3,694,323, the residue is admixed with MDI, partially distilled and converted into a polyurethane. The direct reaction of the residue with a polyol to form the corresponding polyurethane is described in DD-A-296 088, U.S. Pat. No. 4,143,008 and U.S. Pat. No. 4,000,099. However, these processes lead to low-grade products which are usually not usable in the preparation of polyurethanes.

A further possible way of utilizing the residue is hydrolyzing it with water. Such processes have likewise been extensively described. The hydrolysis of the residue is aided by bases or acids. Amines also promote the hydrolysis. The hydrolysis can be used for denaturing the TDI distillation residue, as described, for example, in U.S. Pat. No. 4,091,009. A further possibility is the recovery of TDA which can then be reacted again with phosgene to give TDI. Such processes are described, for example, in DE-A-29 42 678, JP-A-5 8201 751 and DE-A-19 62 598.

All the patents mentioned describe batch processes in which the TDI residue and water first very quickly form a solid phase which slowly reliquefies as the reaction continues. This formation of solid can lead to considerable problems in carrying out the reaction.

DE-A-27 03 313 describes a hydrolysis process which is carried out both batchwise in an autoclave and continuously in a tube reactor. The hydrolysis of the solid TDI residue is carried out using aqueous ammonia solution, solutions of primary or secondary amines in water or aqueous TDA solutions. The use of aqueous TDA solutions is described as less preferred. However, the process described in DE-A-27 03 313 also has disadvantages. For instance, the use of ammonia solution leads to the formation of salts, for example ammonium bicarbonate, ammonium carbonate and salts of organic polyamines which have to be dissociated thermally or removed in some other way. The primary or secondary amines added have to be separated from the recovered TDA. When using aqueous TDA solution, it is necessary to add solubilizers which have to be separated from the hydrolysate after hydrolysis.

U.S. Pat. No. 3,499,035 describes a hydrolysis process in which the TDI residue is first partially hydrolyzed with water and the resulting solid intermediate is reacted with TDA in a second process step. In this process, considerable formation of solid occurs in the first process step.

U.S. Pat. No. 4,654,443 describes a hydrolysis process in which the TDI residue is reacted with TDA in a first process step to form a solid and this intermediate is hydrolyzed with water in a second step. This, too, has the disadvantage that the process comprises two process steps and that TDA has to be added to the reaction mixture. In addition, considerable formation of solids occurs here too.

JP-A-151 270/97 describes a process for the hydrolysis of TDI residues using supercritical or very hot water. Disadvantages of this process are the very high pressure which makes it necessary to use special equipment and also the corrosion problems which result from the use of supercritical water. In addition, a large excess of water has to be employed.

Owing to the problems described, the hydrolysis of TDI distillation residue has hitherto not been implemented on an industrial scale. At present it is still the case that the major part of the distillation residues has to be incinerated, which has a very adverse effect on the economics of TDI production.

It is an object of the present invention to find a reliable hydrolysis process for utilizing the materials in TDI residues that leads to high yields of useful products, in particular TDA, and can readily be combined with existing plants for preparing TDI.

We have found that this object is achieved by carrying out the hydrolysis of the TDI distillation residue in a continuous or semicontinuous process in a backmixed system in the simultaneous presence of hydrolysate and of water. In this way, no solids are formed in the hydrolysis of TDI residues a sentence "FIG. 1 is a schematic generally illustrating the work-up of distillation residue from the synthesis of tolylene diisocyanate.

The present invention accordingly provides a process for hydrolyzing TDI distillation residues by reacting the TDI distillation residue with water in a continuous or semicontinuous process in a backmixed reactor in the presence of hydrolysate. The distillation residue is converted into TDA and carbon dioxide. It is not only the free TDI of the TDI distillation residue which is converted into TDA, but, surprisingly, the other constituents of the TDI distillation residue are also dissociated to a substantial extent, which leads to very high yields of TDA.

For the purposes of the present invention, "hydrolysate" refers to the reaction products of the TDA residue with water.

The hydrolysis should preferably be carried out in the simultaneous presence of hydrolysate and water. In such a procedure, the formation of solids can, surprisingly, be completely avoided. This is preferably effected by intensive backmixing of the reaction mixture.

The hydrolysis is preferably carried out at from 120 to 250° C. and at pressures of from 1 to 50 bar. The pressure should preferably be selected so as to be somewhat higher than the boiling pressure of the product discharged from the hydrolysis reactor at reaction temperature. The mass ratio of TDI residue to water is preferably from 4.8:1 to 1:5, more preferably from 1:1.0 to 1:3.

To rule out formation of solids at the start of the reaction, the reaction vessel should be initially charged with hydrolysate which has, if necessary, been produced beforehand in a separate reactor.

Particularly suitable embodiments of the process of the present invention are the semibatch process and, in particular, the continuous process. As mentioned above, good backmixing of the reaction mixture has to be ensured in order to reliably rule out formation of solids.

In the semibatch process, water and TDI distillation residue are simultaneously metered with an initial charge of hydrolysate in a backmixed reactor, e.g. a stirred tank.

In the continuous process, TDI distillation residue and water are simultaneously metered into a backmixed reactor through which material flows continuously, e.g. a continuous stirred tank, a jet loop, a reaction mixing pump, a pump circuit provided with a static mixer and/or two-fluid mixing nozzle.

To improve the reaction yield, the continuous backmixed reactor can also be configured as a reactor cascade or as a combination of backmixed prereactor and non-backmixed post-reactor, e.g. as a stirred tank with a downstream tube reactor.

In a particularly advantageous embodiment of the present invention, the TDI distillation residue is not metered into the gas phase of the reactor, but directly under the surface of the liquid phase. To avoid blockages at the inlet point, a sufficient flow velocity, preferably greater than 0.5 m/s, has to prevail in the inlet tube.

The TDI distillation residue usually comprises from 0 to 80% by weight of TDI, ureas, tarlike oligomers of TDI, urethanes, isocyanurates, biurets, allophanates, uretdiones, carbodiimides, urethaneimines and other by-products.

The residue which is used for the hydrolysis can be taken from the bottom of the last work-up column or downstream evaporation apparatus. The evaporation apparatus can be, for example, a falling film evaporator as described in NL-A-7109730, a thin film evaporator as described in FR-A-2320-938, a heated tube with a flash pot as described in DT-A-27 25 886, stirred tanks as described in U.S. Pat. No. 3,405,040, a heated ball mill as described in U.S. Pat. No. 3,457,291, a single- or twin-screw extruder as described in EP-A-38 502 and EP-A-463, a fluidized bed as described in DT-A-29 15 830, paddle dryers, a two-phase helix tube or any other apparatus. Neither the TDI content nor the consistency of the TDI residue, i.e. whether it is liquid or solid, nor therefore the type of evaporation apparatus restrict the applicability of the hydrolysis process of the present invention. However, for better handling of the TDI residue, it is advantageous if it is pumpable.

To further improve the handleablity of the TDI distillation residue it can also be taken up in a suitable organic solvent which does not react with the residue, e.g. toluene, N-methylpyrrolidone, DMF, monochlorobenzene, dichlorobenzene and others.

The hydrolysis can be aided by the use of bases such as alkali metal hydroxides and/or alkaline earth metal hydroxides, e.g. sodium hydroxide, potassium hydroxide, magnesium hydroxide, calcium hydroxide, magnesium oxide, calcium oxide, ammonia or amines, or acids such as hydrochloric acid, hydrobromic acid or sulfuric acid.

When using alkali metal hydroxides, they are preferably used in an amount of from 0.5 to 5.0% by weight, based on the reaction mixture.

The use of catalysts customarily used for the dissociation of urethanes, e.g. solids of iron, zinc, tin and zirconium, likewise aids the hydrolysis.

The hydrolysate is taken continuously from the hydrolysis reactor and worked up. In the preferred solvent-free process, the hydrolysate consists of a single phase. The water which has been used in excess is first separated off by distillation and the TDA is subsequently separated off by distillation. When using water-soluble solvents, a major part of the water can be separated off by carrying out a phase separation beforehand. The water which has been separated off can in either case be returned to the hydrolysis.

The TDA obtained by means of the hydrolysis can, after appropriate purification and work-up, either be introduced into the phosgenation reactor of the TDI process or can be added to the reaction mixture leaving the hydrogenation reactor in the preparation of TDA by hydrogenation of dinitrotoluene. The latter process variant has the advantage that the work-up step after the hydrolysis can be simplified or possibly dispensed with entirely. The by-products of the hydrolysis can then be removed from the process together with the TDA tar in the TDA work-up step.

Alternatively, the hydrolysis product after removal of water can also be used, without further work-up or after removal of by-products, for preparing polyetherols by molecular addition of alkylene oxides. It is naturally also possible to react the purified TDA with alkylene oxides to form polyetherols.

The invention is illustrated by the following examples.

EXAMPLE 1

345 g/h of deionized water and 350 g/h of a melt of a distillation residue from the preparation of TDI by reaction of TDA with phosgene which, according to SFC analysis (Supercritical Fluid Chromatography), still contained about 20% by weight of free TDI were introduced continuously via an immersed tube into a stirred tank reactor having a capacity of 7 l. The reaction was carried out at 200° C. and a constant pressure of 30 bar and a constant fill level of 5 l. The gas evolution measured by means of a gas meter was 68.6 l/h. The liquid output rate was 568 g/h. The analysis of the reactor output indicated a TDA content of 34.1% by weight, corresponding to a TDA yield of 55 g of TDA per 100 g of TDI distillation residue used. The TDA was separated from the reaction mixture by distillation.

EXAMPLE 2

34.6 g/h of deionized water and 70.3 g/h of a 50% strength by weight solution of the TDI distillation residue described in Example 1 in toluene were introduced continuously via an immersed tube into a stirred tank reactor having a capacity of 2 l. The reaction was carried out at 200° C. and a constant pressure of 25 bar and a constant fill level of 800 ml. The gas evolution measured by means of a gas meter was 7.5 l/h. The liquid output rate was 93g/h. The analysis of the reactor output indicated a TDA content of 20.6% by weight, corresponding to a TDA yield of 54.5% of TDA per 100 g of TDI distillation residue used.

EXAMPLE 3

33.9 g/h of a 5% strength aqueous sodium hydroxide solution and 74.4 g/h of a 50% strength by weight toluene solution of the TDI distillation residue described in Example 1 were introduced continuously via an immersed tube into a stirred tank reactor. The reaction was carried out at 195° C. and a constant pressure of 25 bar and a constant fill level of 800 ml. The gas evolution measured by means of a gas meter was 8.9 l/h. The liquid output rate was 89.4 g/h. The analysis of the reactor output indicated a TDA content of 25.6% by weight, corresponding to a TDA yield of 61.5 g of TDA per 100 g of TDI distillation residue used.

EXAMPLE 4

937.4 g of TDI distillation residue which, according to SFC analysis, still contained about 20% by weight of free TDI was evaporated to dryness at 15 mbar and 240° C. in a reaction mixer provided with rotating parts. This gave 458.6 g of distillate having a TDI content of 97.3% by weight and 445.7 g of a free-flowing, non-dusting residue. Neither TDI nor NCO groups could be detected in the residue. The balance error of 33 g can be explained by the gaseous dissociation products formed under these conditions.

70 g/h of an aqueous suspension which contained 50% by weight of the TDI- and NCO-free residue described in Example 4 and was at room temperature were metered continuously via an immersed tube into a stirred tank reactor as described in Example 2. The stirred tank reactor was operated continuously at 200° C. The output of 57.4 g/h contained 38.64% by weight of TDA, corresponding to a TDA yield of 63.4 g of TDA per 100 g of TDI distillation residue used.

EXAMPLE 5 (comparison)

400 g of milled TDI distillation residue and 400 g of deionized water were placed as a suspension in a stirred reactor having a capacity of 2 l. While heating the mixture to the final reaction temperature of 200° C., the formation of a firm, paste-like mass which could not be stirred and reacted only slowly could be observed through a sight glass.

EXAMPLE 6 (comparison)

300 g of water were placed in a reactor as described in Example 2 and 600 g of a 50% strength by weight solution of the TDI distillation residue in toluene were metered in at a rate of 2.5 g/h. The reactor was operated at 200° C. and a pressure of 25 bar. Immediately the toluene solution of TDI distillation residue was metered in, the formation of solid commenced. The formation of solid was so great that the reactor could no longer be mixed. Only after about 3 hours did the solid formed slowly break down.

EXAMPLE 7 (comparison)

600 g of a 50% strength by weight solution of the TDI distillation residue in toluene were placed in a reactor as described in Example 2 and 300 g of water were metered in at a rate of 1.25 g/h. The reactor was operated at 200° C. and a pressure of 25 bar. Immediately the water was metered in, the formation of solid commenced. The formation of solid was so great that the reactor could no longer be mixed. Only after 1.5 hours had the solid formed broken down.

EXAMPLE 8

400 g of fully reacted hydrolysis product from Example 2 were placed in a reactor as described in Example 2 and a 50% strength by weight solution of the TDI distillation residue in toluene was metered in at a rate of 2.5 g/h at the same time as water was metered in at a rate of 1.25 g/h. The reactor was operated at 200° C. and a pressure of 25 bar. Under these conditions, there was no formation of solid whatsoever.

EXAMPLE 9

840 g/h of water and 389 g/h of the distillation residue described in Example 1 were metered continuously into a reactor as described in Example 1. The reaction was carried out at 230° C. and a pressure of 35 bar and a constant fill level of 5 l. The gas evolution measured by means of a gas meter was 95 l/h. The liquid output rate was 1056 g/h. The analysis of the reactor output indicated a TDA content of 23.2% by weight, corresponding to a TDA yield of 63.1 g per 100 g of TDI distillation residue used.

EXAMPLE 10

830 g/h of a 3% strength by weight aqueous sodium hydroxide solution and 974 g/h of the distillation residue described in Example 1 were metered continuously into a reactor as described in Example 1. The reaction was carried out at 222° C. and a pressure of 35 bar and a constant fill level of 5 l. The gas evolution measured by means of a gas meter was 241 l/h. The liquid output rate was 1368 g/h. The analysis of the reactor output indicated a TDA content of 47.8% by weight, corresponding to a TDA yield of 67.1 g per 100 g of TDI distillation residue used.

We claim:

1. A process for working up tolylene diisocyanate (TDI) distillation residues from the synthesis of TDI comprising providing the TDI distillation residues, and reacting the TDI distillation residues with water in a continuous or semicontinuous process in a backmixed reactor in the presence of reaction products of toluenediamine (TDA) residues and water.

2. A process as claimed in claim 1, wherein the reaction is carried out in a semicontinuous process in a stirred tank by initially charging the tank with the reaction products of the distillation residue and water, adding water and TDI distillation residues to the reaction products of the TDA residues and water, and working up the reaction products of the TDA residues and water after the reaction.

3. A process as claimed in claim 1, wherein the reaction is carried out in a continuous process in a backmixed reactor.

4. A process as claimed in claim 3, wherein the backmixed reactor is a stirred tank, a stirred tank cascade, a reaction mixing pump, a pumped circuit provided with a static mixer and/or a two-fluid mixing nozzle, a jet loop reactor or a jet nozzle reactor.

5. A process as claimed in claim 1, wherein the hydrolysis is carried out at from 120° C. to 250° C.

6. A process as claimed in claim 1, wherein the hydrolysis is carried out at from 170° C. to 250° C.

7. A process as claimed in claim 1, wherein the hydrolysis is carried out at a pressure in the range from 1 to 50 bar and the pressure is higher than the boiling pressure of the product discharged from the reactor at a reaction temperature in the range from 120 to 250° C.

8. A process as claimed in claim 1, wherein the TDI distillation residues are introduced into the liquid phase of the reactor.

9. A process as claimed in claim 1, wherein the hydrolysis is carried out in the presence of at least one base selected from the group consisting of alkali metal hydroxides, alkaline earth metal hydroxides, ammonia amines, and combinations thereof.

10. A process as claimed in claim 1, wherein the mass ratio of TDI distillation residues introduced to water introduced in the hydrolysis is from 4.8:1 to 1:5.

11. A process as claimed in claim 1, wherein the mass ratio of TDI distillation residue introduced to water introduced is from 1:1.0 to 1:3.

12. A process as claimed in claim 1, wherein the TDI distillation residues are dissolved in an organic solvent which does not react with the TDI residues, wherein the organic solvent is selected from the group consisting of toluene, N-methylpyrrolidone, dimethylformamide, monochlorobenzene, dichlorobenzene, and combinations thereof.

13. A process as claimed in claim 1, wherein the reaction products of the TDA residues and water are, without further work-up, reacted with alkylene oxides to form polyether alcohols.

14. A process for preparing TDI by reacting TDA with phosgene and subsequently separating off the resulting TDI by distillation, which comprises subjecting the remaining distillation residues to a hydrolysis as claimed in claim 1, separating the TDA from the reaction products of the TDA residues and water and returning this to the phosgenation.

15. A process for working up distillation residues from the synthesis of tolylene diisocyanate comprising providing TDI distillation residue, and reacting the TDI distillation residues with water in a continuous or semicontinuous process in a backmixed reactor in the presence of the reaction products of the TDA residues and water, wherein the reaction is carried out in the presence of salts of iron, zinc, tin or zirconium.

16. A process as claimed in claim 1, wherein the hydrolysis is carried out in the presence of at least one acid selected from the group consisting of hydrochloric acid, hydrobromic acid, sulfuric acid, and combinations thereof.

* * * * *